United States Patent
Fenech et al.

(10) Patent No.: US 12,392,396 B2
(45) Date of Patent: *Aug. 19, 2025

(54) SYSTEMS AND METHODS FOR A COMPACT REMOTE CENTER MANIPULATOR

(71) Applicant: INTUITIVE SURGICAL OPERATIONS, INC., Sunnyvale, CA (US)

(72) Inventors: Carolyn M. Fenech, San Jose, CA (US); Daniel H. Gomez, Los Gatos, CA (US); Jason N. Stamatelaky, Tracy, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/605,516

(22) Filed: Mar. 14, 2024

(65) Prior Publication Data

US 2024/0216095 A1  Jul. 4, 2024

Related U.S. Application Data

(63) Continuation of application No. 17/330,672, filed on May 26, 2021, now Pat. No. 11,957,427.
(Continued)

(51) Int. Cl.
- *F16H 7/08* (2006.01)
- *A61B 34/00* (2016.01)
- *B25J 9/10* (2006.01)

(52) U.S. Cl.
CPC ............... *F16H 7/08* (2013.01); *A61B 34/71* (2016.02); *B25J 9/104* (2013.01); *B25J 9/106* (2013.01); *F16H 2007/0865* (2013.01)

(58) Field of Classification Search
CPC .......... A61B 34/71; A61B 34/35; B25J 9/104; B25J 9/106
See application file for complete search history.

(56) References Cited

U.S. PATENT DOCUMENTS

| | | | | |
|---|---|---|---|---|
| 5,794,487 A | * | 8/1998 | Solomon | B25J 9/106 474/271 |
| 6,634,851 B1 | * | 10/2003 | Bonora | H01L 21/68707 414/744.3 |

(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Bobby Rushing, Jr.
(74) *Attorney, Agent, or Firm* — Haynes & Boone, LLP.

(57) ABSTRACT

A surgical manipulator linkage assembly may comprise a linkage arm that includes a first pulley and a second pulley. Each of the first pulley and the second pulley comprise a first drive track and a second drive track. The first drive track and the second drive track are substantially co-planar, and the first drive track extends at least partially around the second drive track. The linkage arm also includes a first drive member section extending between the first drive tracks of the first pulley and the second pulley. The linkage arm also includes a second drive member section extending between the second drive tracks of the first pulley and the second pulley. The first drive member section is wound around the first pulley in a first tensile direction and the second drive member section is wound around the first pulley in a opposite second tensile direction.

20 Claims, 15 Drawing Sheets

Related U.S. Application Data

(60) Provisional application No. 63/034,733, filed on Jun. 4, 2020.

(56) References Cited

U.S. PATENT DOCUMENTS

| | | |
|---|---|---|
| 7,736,254 B2 | 6/2010 | Schena |
| 9,068,628 B2 | 6/2015 | Solomon et al. |
| 9,295,524 B2 | 3/2016 | Schena et al. |
| 10,143,525 B2 | 12/2018 | Schena et al. |
| 11,957,427 B2 | 4/2024 | Fenech et al. |
| 2017/0020615 A1 | 1/2017 | Koenig et al. |
| 2018/0079074 A1 | 3/2018 | Devengenzo et al. |
| 2018/0079090 A1 | 3/2018 | Koenig et al. |
| 2021/0378771 A1 | 12/2021 | Fenech et al. |

\* cited by examiner

SYSTEMS AND METHODS FOR A COMPACT REMOTE CENTER MANIPULATOR

CROSS-REFERENCE TO RELATED APPLICATIONS

This application is a continuation of U.S. patent application Ser. No. 17/330,672 filed May 26, 2021 which claims priority to and the benefit of U.S. Provisional Application 63/034,733 filed Jun. 4, 2020, each of which is incorporated by reference herein in its entirety.

FIELD

The present disclosure is directed to systems and methods for robotically-assisted manipulation of an instrument about a remote center of manipulation using a compact manipulator.

BACKGROUND

Minimally invasive medical techniques are intended to reduce the amount of tissue that is damaged during diagnostic or surgical procedures, thereby reducing patient recovery time, discomfort, and harmful side effects. Such minimally invasive techniques may be performed through one or more surgical incisions or through natural orifices in a patient anatomy. Through these incisions or natural orifices, clinicians may insert minimally invasive medical instruments (including surgical, diagnostic, therapeutic, or biopsy instruments) to reach a target tissue location. Minimally invasive robotically-assisted and computer-assisted medical systems have been developed to increase a surgeon's dexterity and avoid some of the limitations on traditional minimally invasive techniques. Robotically-assisted medical systems allow a user to control medical instruments via a manipulator. The manipulator may include two or more links coupled together by one or more joints. The joints may include actively controlled joints. The joints may also include passive joints, which are not actively controlled, but comply with movement of actively controlled joints. Such active and passive joints may be revolute or prismatic joints.

Minimally invasive telesurgical systems allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments.

In some robotically-assisted medical systems, multiple manipulators may be mounted to a common platform which may be unwieldy or make some aspects of patient access difficult. For some medical procedures, more compact, more portable, and lighter weight manipulators may be suitable to improve patient access and procedure efficiency.

SUMMARY

Examples of the invention are summarized by the claims that follow the description.

Consistent with some examples, a manipulator for a surgical instrument may comprise an instrument holder coupled with the surgical instrument and rotatable in a plane that passes through a remote center. The manipulator may also comprise a linkage assembly coupled to the instrument holder to limit motion of the instrument holder to rotation about an axis that intersects the remote center. The linkage assembly may comprise a first linkage arm comprising first and second pulleys. Each pulley may comprise first and second drive tracks which are substantially co-planar. The first linkage arm may also comprise a first drive member section extending between the first drive tracks of the pulleys and a second drive member section extending between the second drive tracks of the pulleys. The first drive member section may be wound around the first pulley in a first direction and the second drive member section may be wound around the first pulley in an opposite direction. The first drive member section and the second drive member section may each comprise at least one selected from the group consisting of belts, cables, and chains.

In another example, a manipulator for articulating a surgical instrument may comprise an instrument holder configured to couple with the surgical instrument and to rotate in a plane that passes through a remote center of manipulation. The manipulator may also comprise a linkage assembly coupled to the instrument holder and configured to produce motion of the instrument holder that is limited to rotation about a first axis that intersects the remote center of manipulation. The linkage assembly may comprise a first linkage arm comprising a first pulley and a second pulley. Each of the first pulley and the second pulley may include an outer drive track and an inner drive track nested within the outer drive track. The first linkage arm may also comprise a first drive member section extending between the inner drive tracks of the first pulley and the second pulley and a second drive member section extending between the outer drive tracks of the first pulley and the second pulley. Rotation of the first pulley in a first direction causes a rotation of the second pulley in the first direction, and rotation of the first pulley in a second direction causes a rotation of the second pulley in the second direction. The first drive member section and the second drive member section may each comprise at least one selected from the group consisting of belts, cables, and chains.

In another example a method may comprise rotating a first linkage arm in a first direction. The first linkage arm may house a first pulley and a second pulley. The first pulley may be coupled to the second pulley by a first drive member section and a second drive member section. Each of the first pulley and the second pulley may comprise a first drive track and a second drive track. The first drive track and the second drive track may be substantially co-planar. The first drive member section may extend between the first drive tracks of the first pulley and the second pulley and the second drive member section may extend between the second drive tracks of the first pulley and the second pulley. The method may further comprise winding the first drive member section on the first drive track of the first pulley as the first linkage arm is rotated in the first direction and unwinding the second drive member section from the second drive track of the first pulley as the first linkage arm is rotated in the first direction. The method may also comprise operating a linkage assembly comprising the first linkage arm to produce motion of an instrument holder that is limited to rotation about a first axis that intersects a remote center of manipulation.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 3:
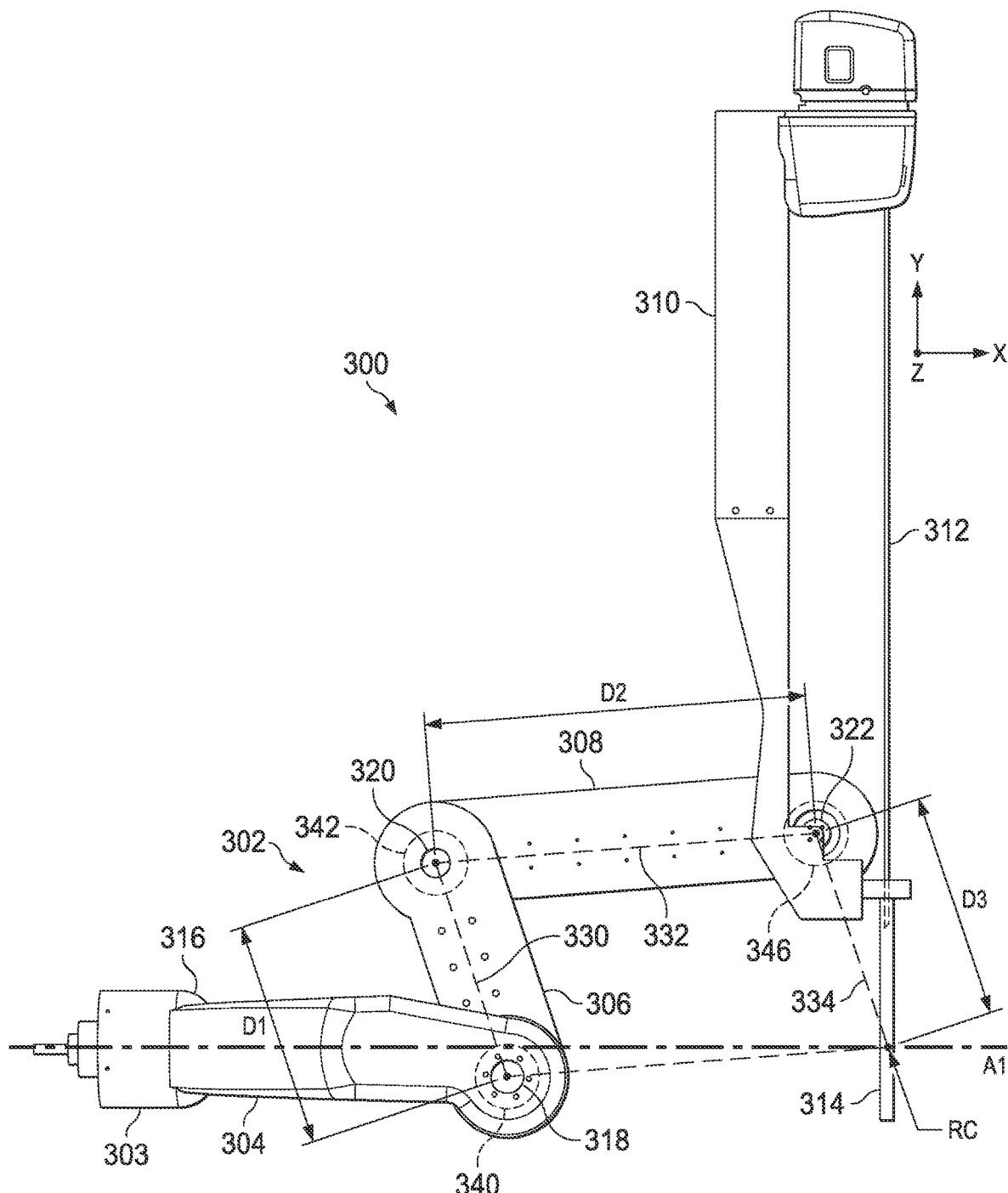
FIG. 3 is a side view of a manipulator assembly according to some embodiments.
Figure 4:
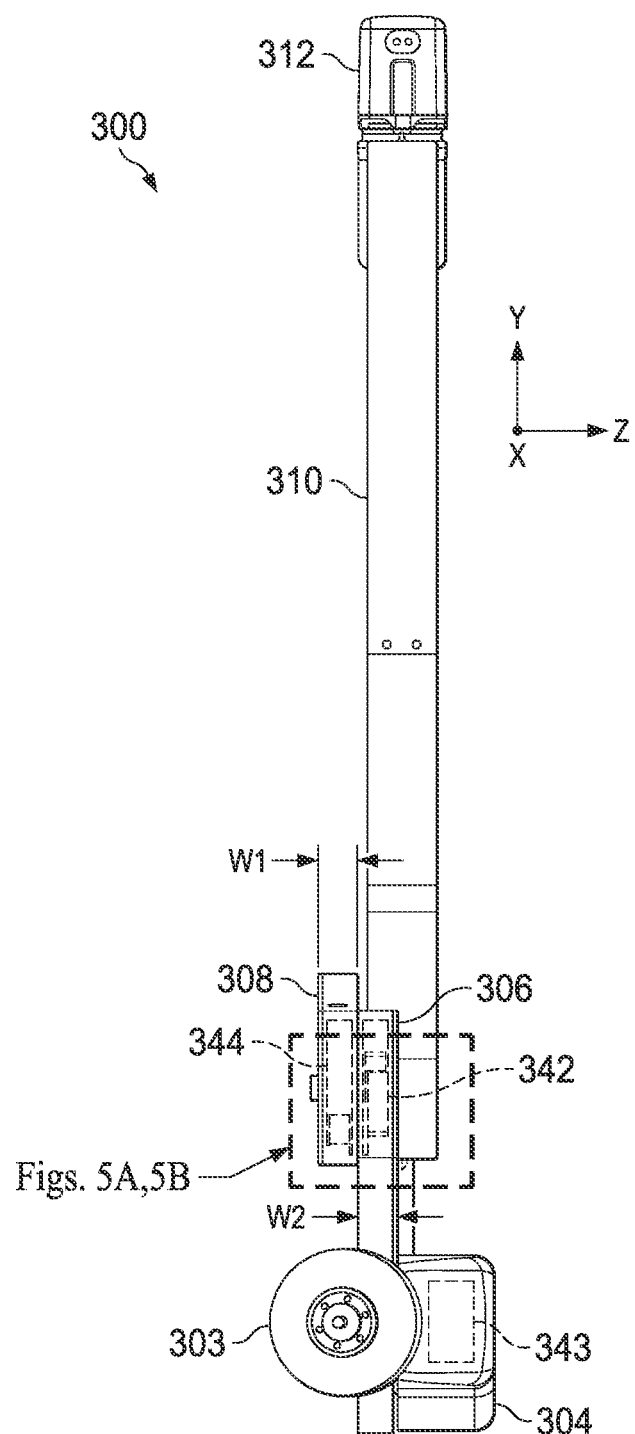

FIG. 4. is a rear view of the manipulator assembly of FIG. 3.

Figure 5A:
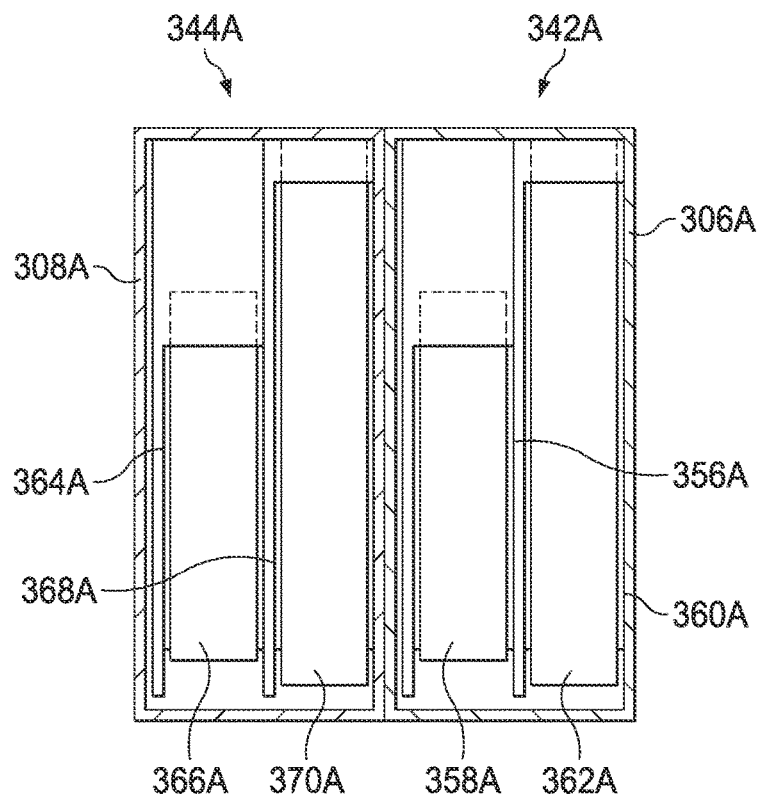

FIG. 5A is a view of a portion of FIG. 4 according to some embodiments.

Figure 5B:
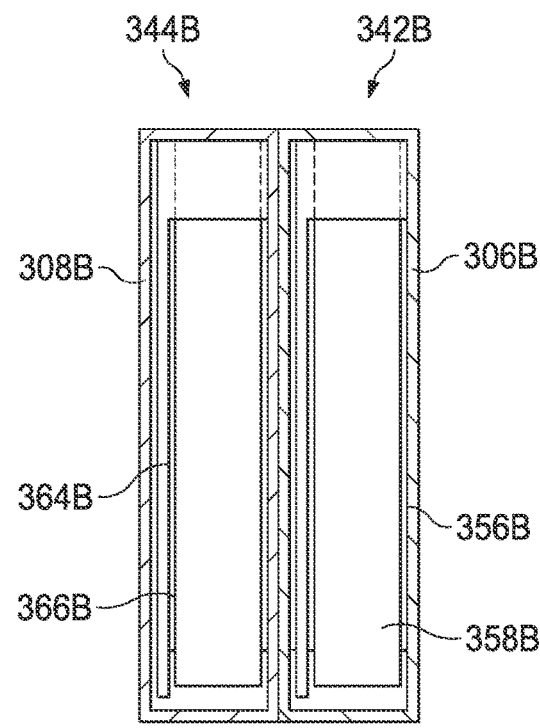

FIG. 5B is a view of a portion of FIG. 4 according to some embodiments.

Figure 6:
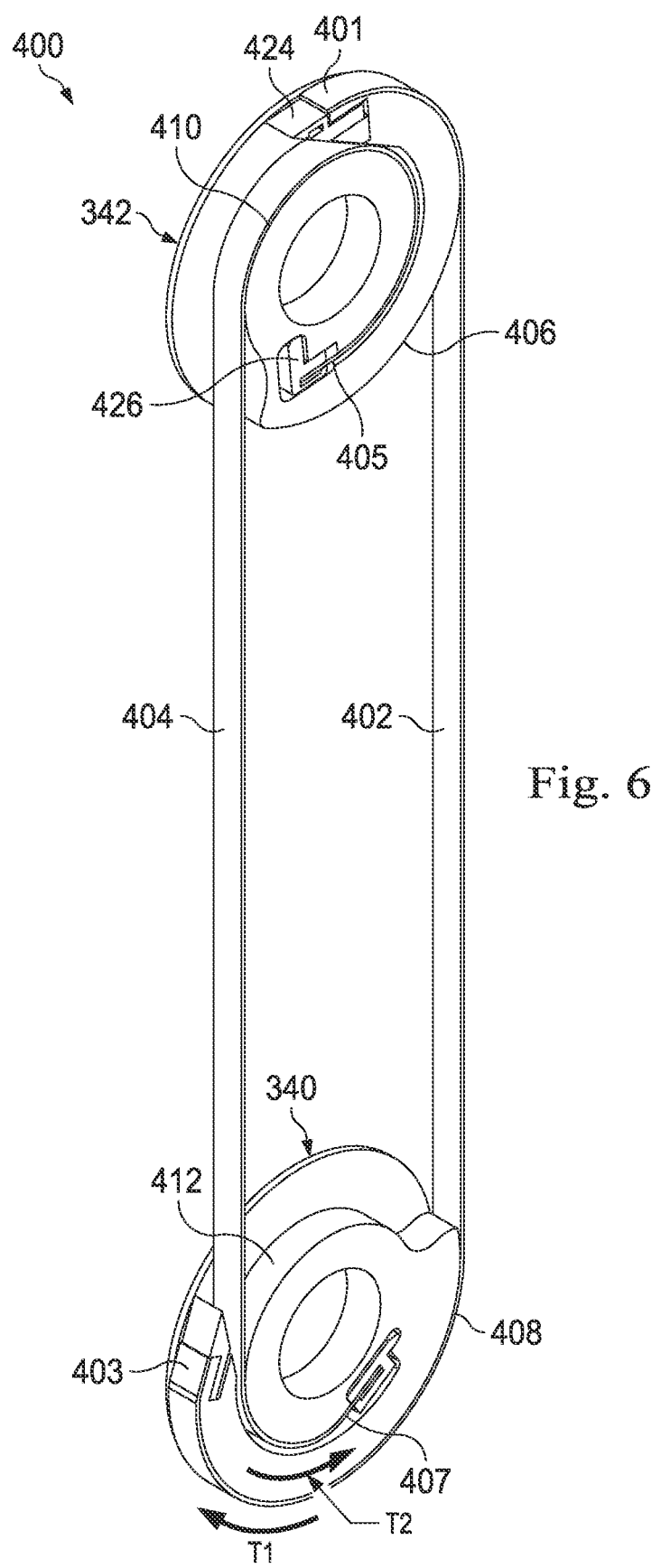

FIG. 6 illustrates a manipulator transmission system according to some embodiments.

Figure 7A:
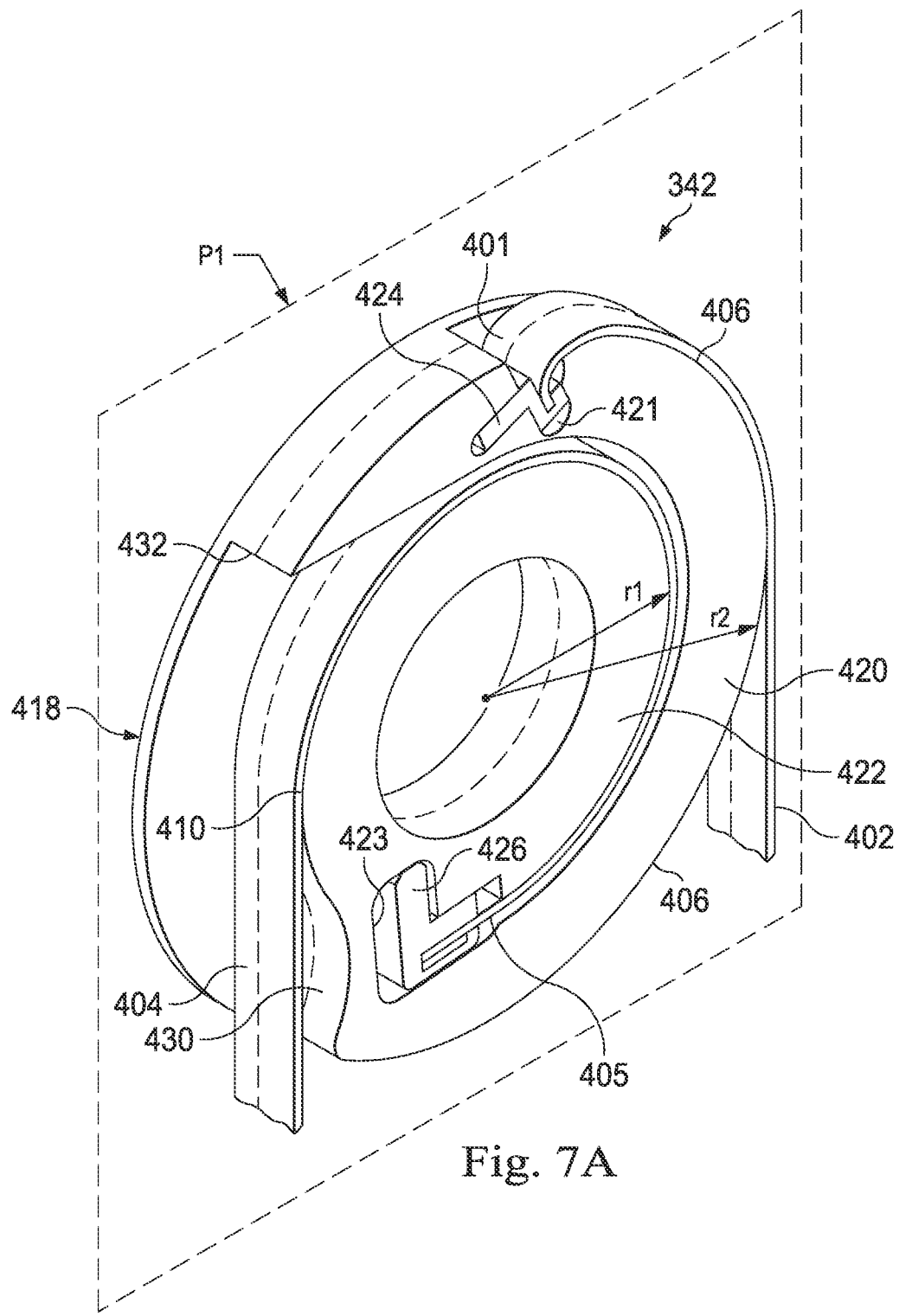

FIG. 7A illustrates a perspective view of a pulley component of the manipulator transmission system of FIG. 6, according to some embodiments.

Figure 7B:
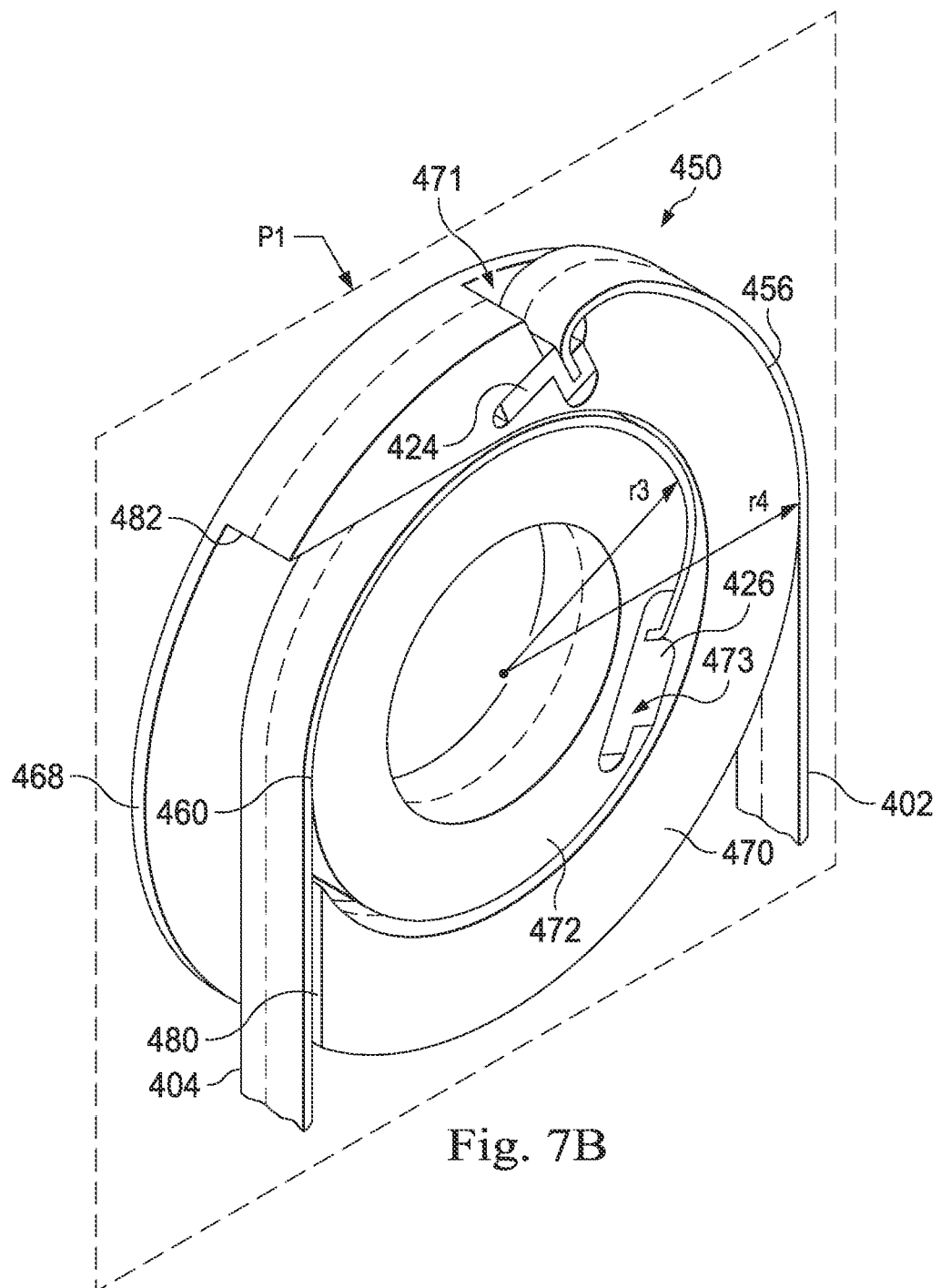

FIG. 7B illustrates a perspective view of a pulley component of the manipulator transmission system according to some embodiments.

Figure 8A:
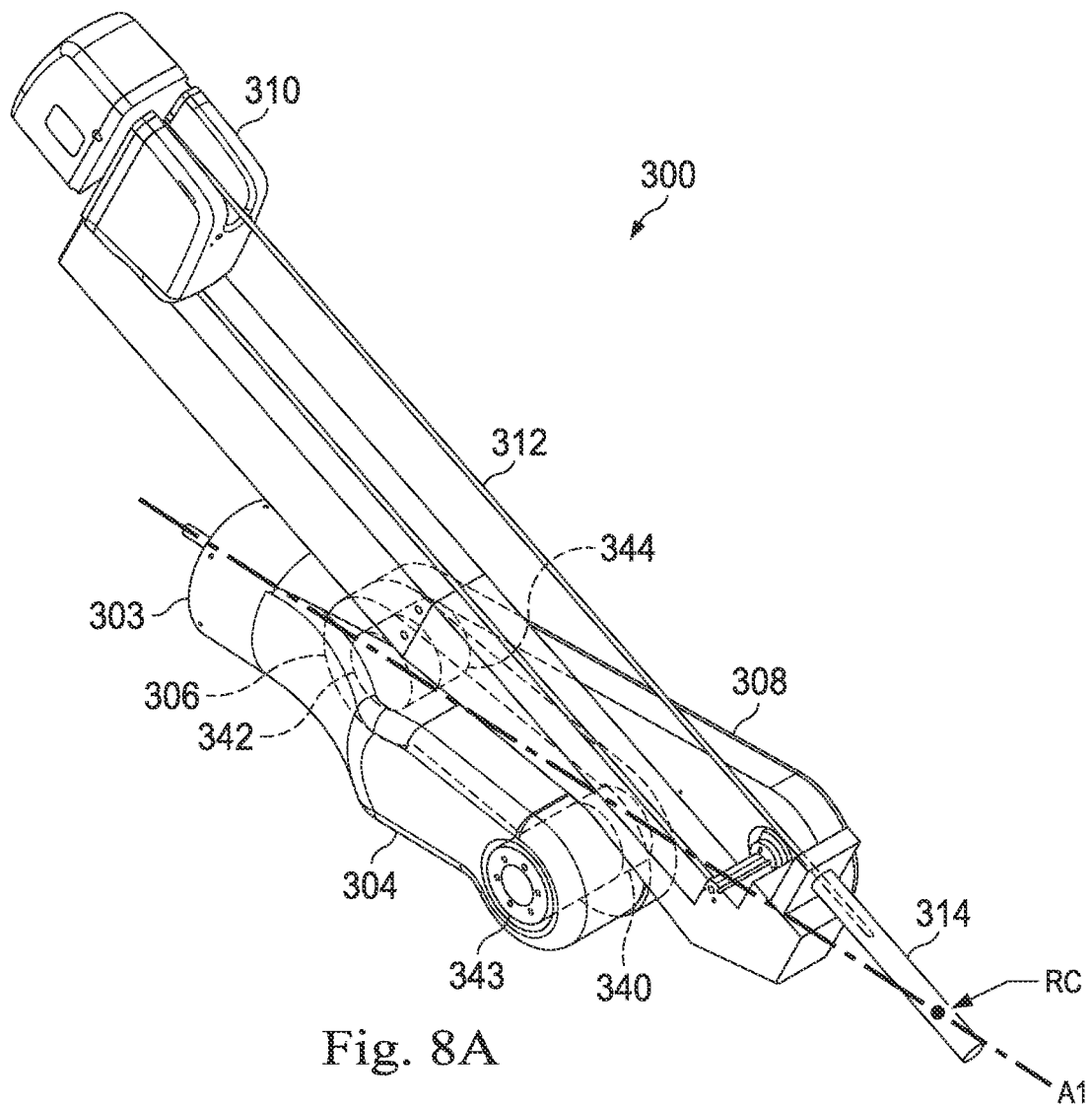

FIG. 8A is a perspective view of a manipulator assembly in a retracted configuration according to some embodiments.

Figure 8B:
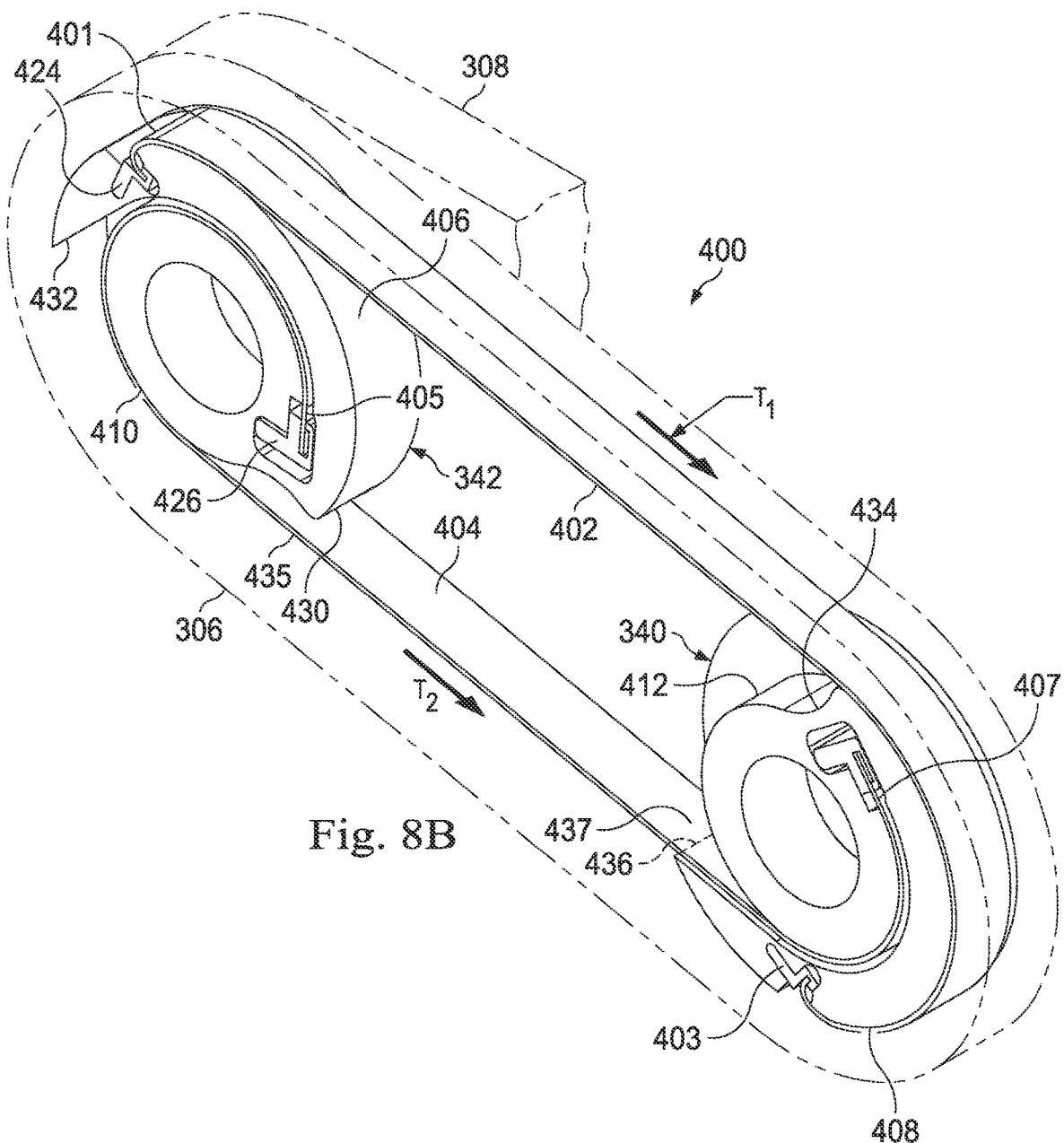

FIG. 8B is a perspective view of the manipulator transmission system of the manipulator assembly of FIG. 8A in the retracted configuration according to some embodiments.

Figure 9A:
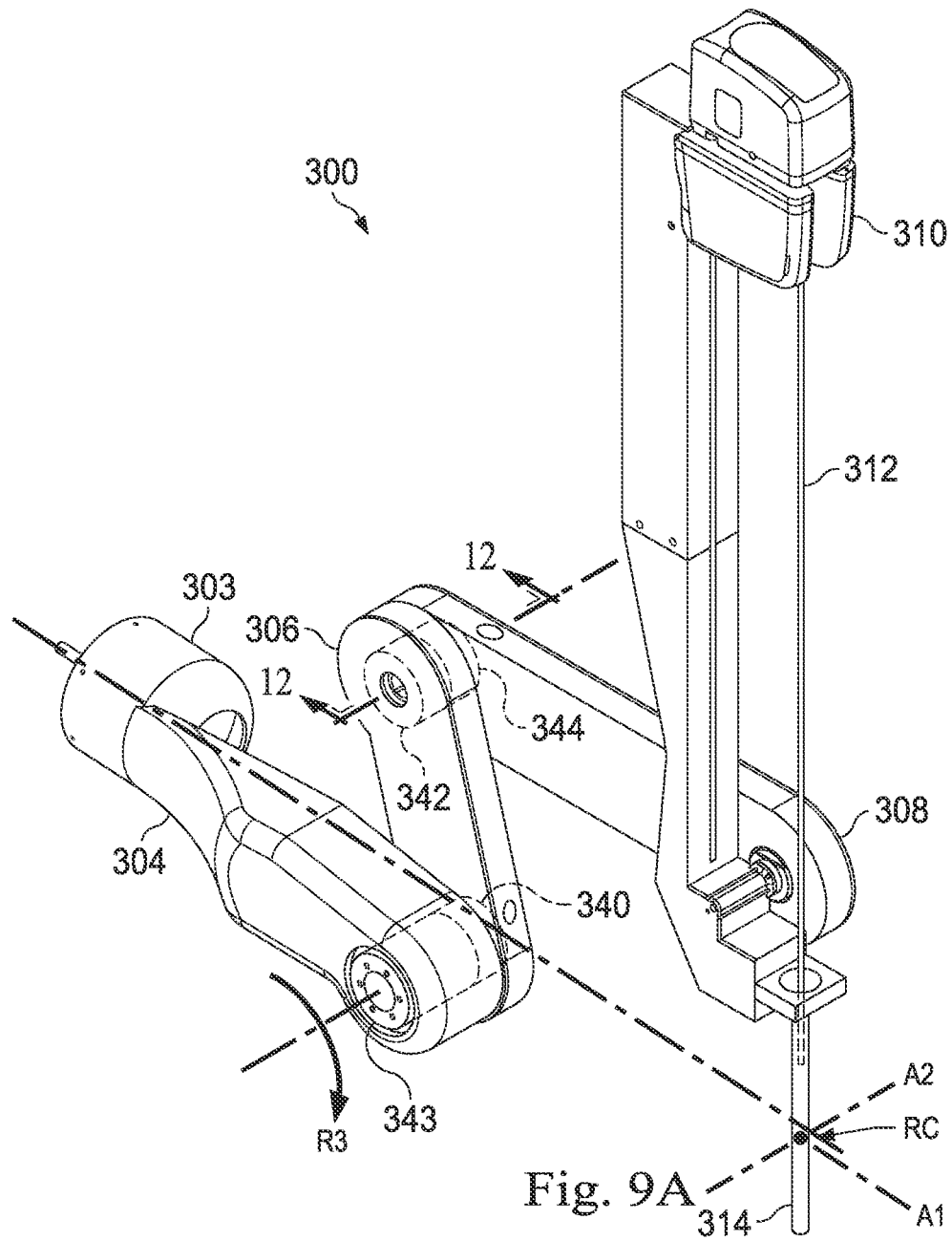

FIG. 9A is a perspective view of a manipulator assembly in a partially extended or mid-extension configuration according to some embodiments.

Figure 9B:
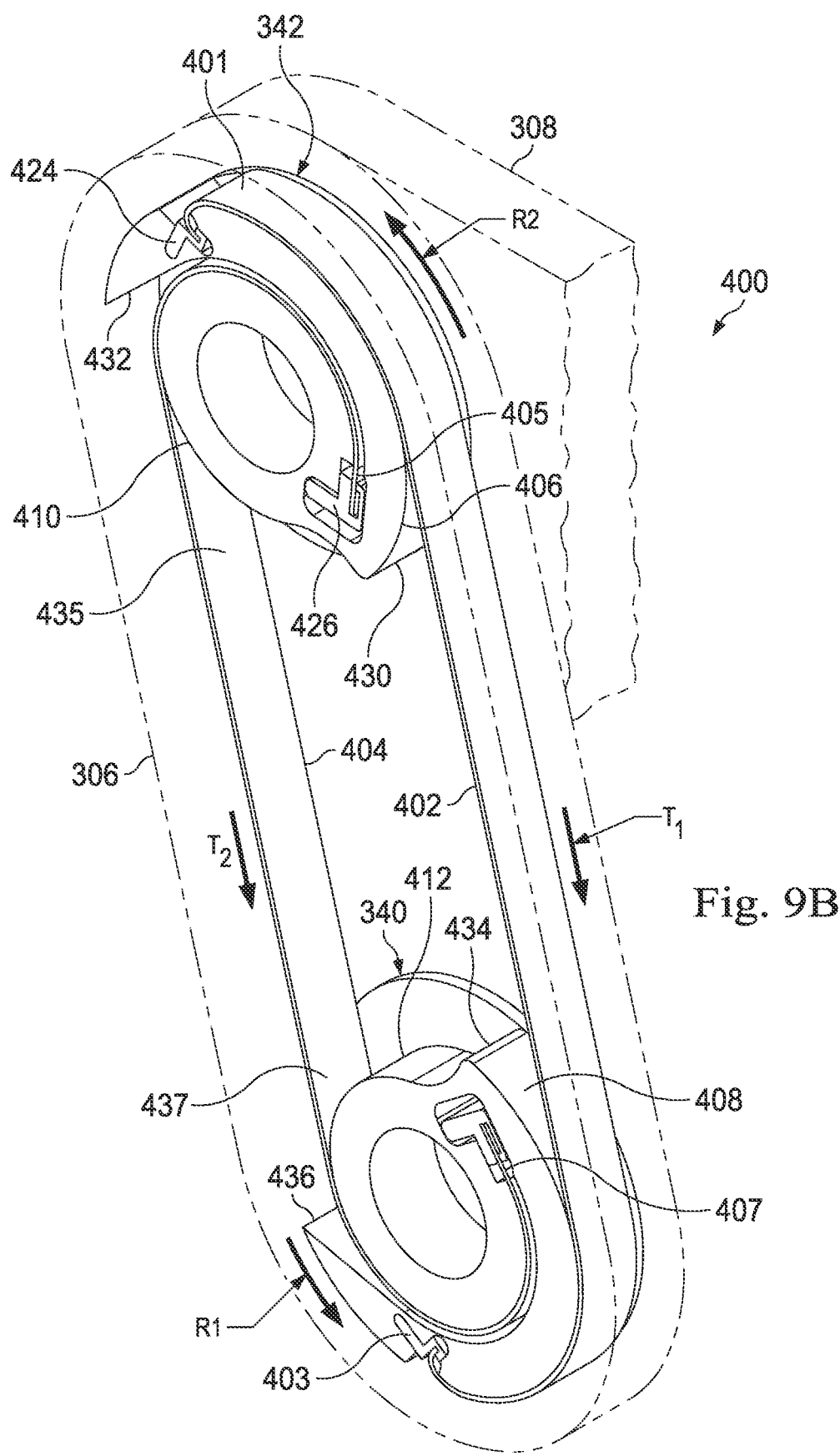

FIG. 9B is a perspective view of the manipulator transmission system of the manipulator assembly of FIG. 9A in the partially extended or mid-extension configuration according to some embodiments.

Figure 10A:
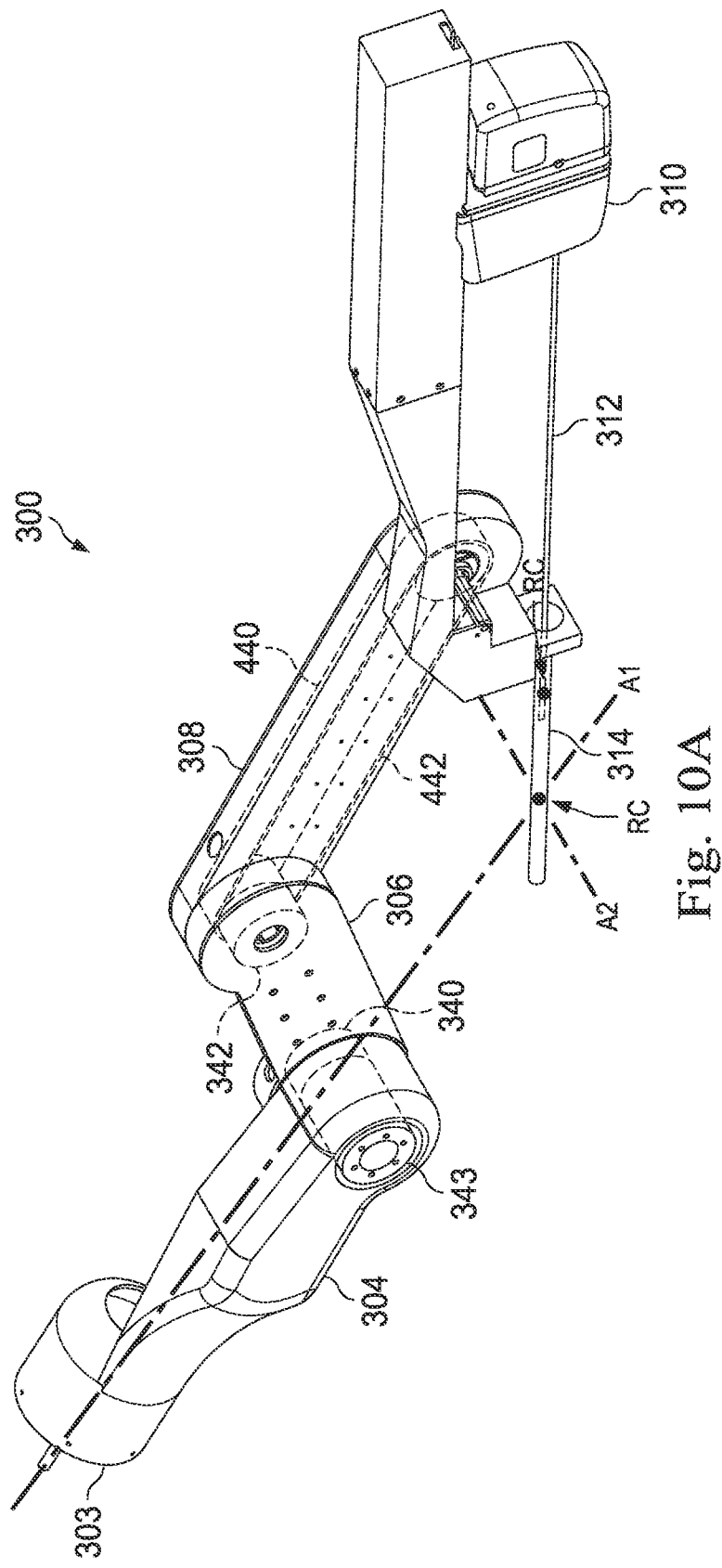

FIG. 10A is a perspective view of a manipulator assembly in an extended configuration according to some embodiments.

Figure 10B:
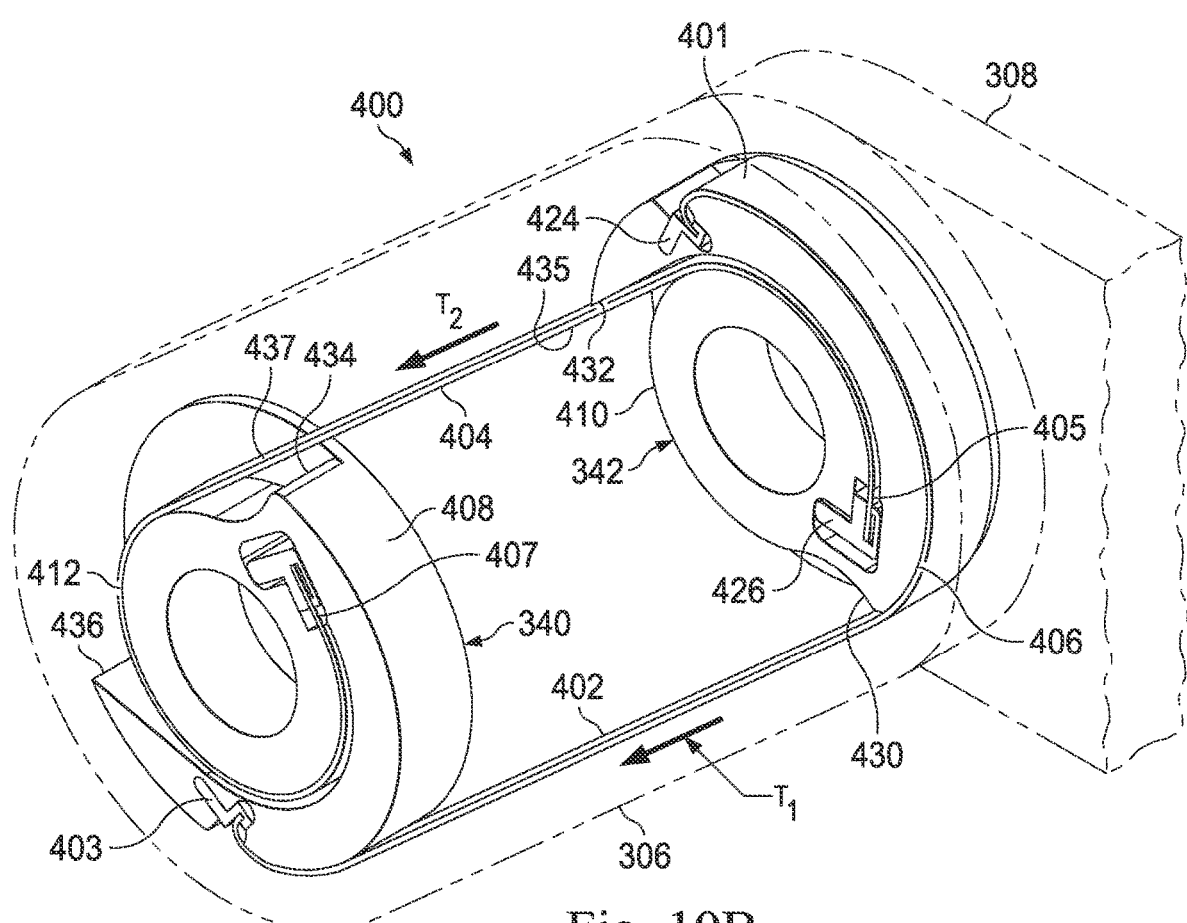

FIG. 10B is a perspective view of the manipulator transmission system of the manipulator assembly of FIG. 10A in the extended configuration according to some embodiments.

Figure 11:
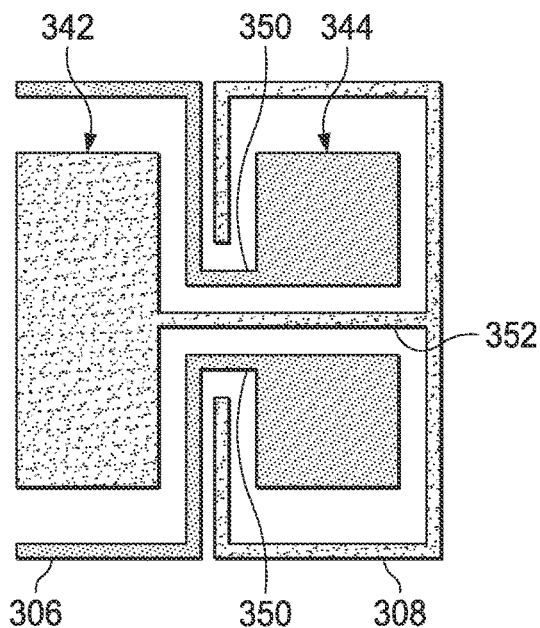

FIG. 11 illustrates a cross-sectional view of the joint between two linkage arms according to some embodiments.

Figure 12:
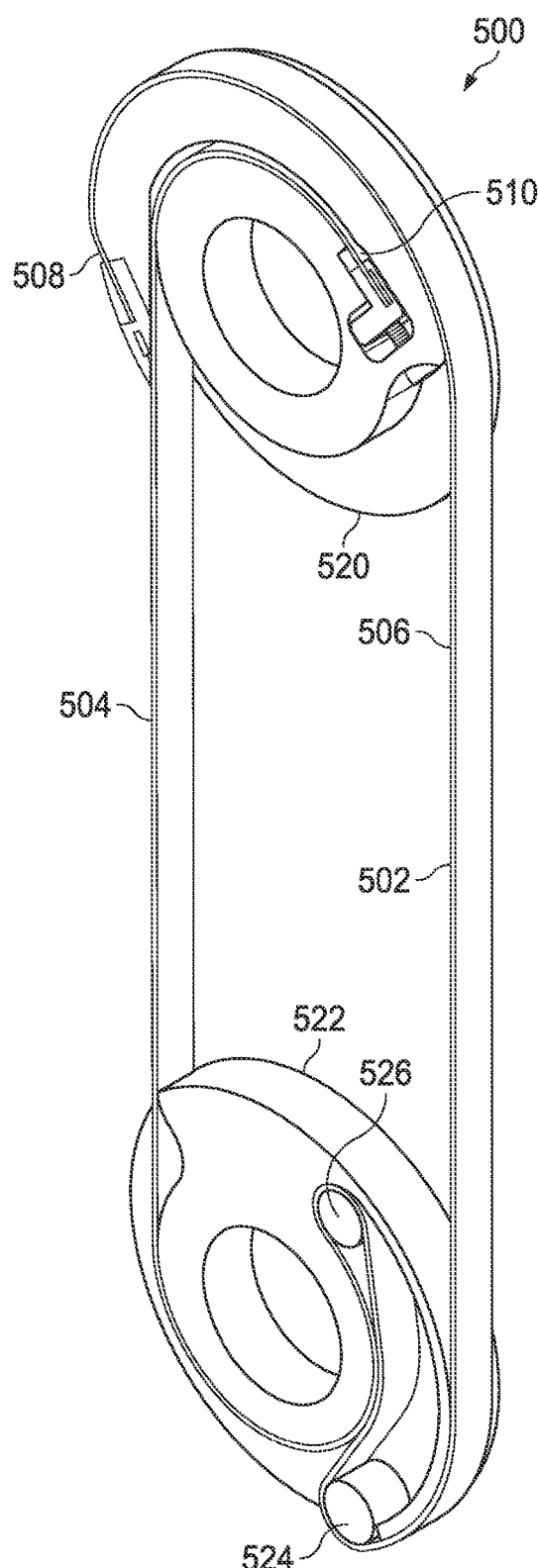

FIG. 12 illustrates a manipulator transmission system according to some embodiments.

Figure 13:
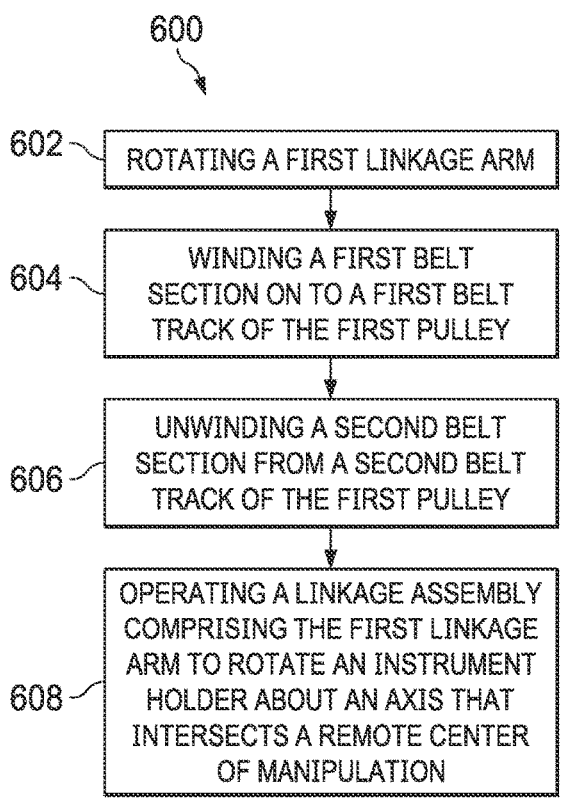

FIG. 13 illustrates a method for operating a manipulator transmission system according to some embodiments.

Embodiments of the present disclosure and their advantages are best understood by referring to the detailed description that follows. It should be appreciated that like reference numerals are used to identify like elements illustrated in one or more of the figures for purposes of illustrating but not limiting embodiments of the present disclosure.

DETAILED DESCRIPTION

Figure 1:
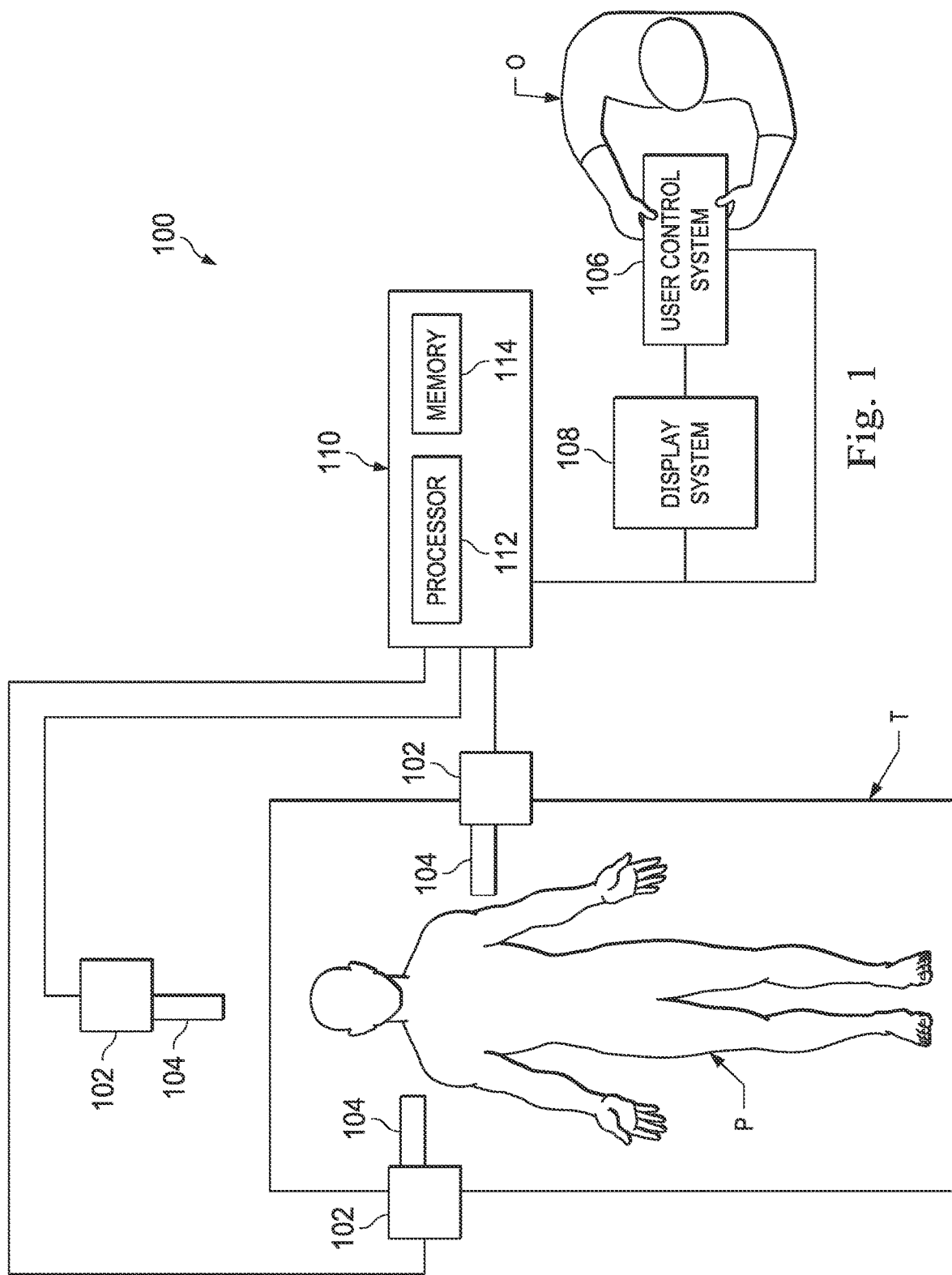
FIG. 1 is a simplified diagram of a robotically-assisted medical system according to some embodiments.

FIG. 1 is a simplified diagram of a robotically-assisted medical system 100 according to some embodiments. In some embodiments, system 100 may be suitable for use in therapeutic and diagnostic procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems. For example, the systems, instruments, and methods described herein may be used for non-medical purposes including industrial uses, general robotic uses, and manipulating non-tissue work pieces.

As shown in FIG. 1, system 100 generally includes a plurality of manipulator assemblies 102. Although three manipulator assemblies 102 are illustrated in the embodiment of FIG. 1, in other embodiments, more or fewer manipulator assemblies may be used. The exact number of manipulator assemblies will depend on the medical procedure and the space constraints within the operating room, among other factors.

The manipulator assembly 102 is used to operate a medical instrument 104 (e.g., a surgical instrument or an image capturing device) in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or located near an operating or surgical table T. In embodiments in which a plurality of manipulator assemblies 102 are employed, one or more of the manipulator assemblies 102 may support surgical instruments, and another of the manipulator assemblies 102 may support an image capturing device, such as a monoscopic or stereoscopic endoscope.

A user control system 106 allows an operator (e.g., a surgeon or other clinician as illustrated in FIG. 1) to view the interventional site and to control manipulator assembly 102. In some examples, the user control system 106 is a surgeon console, which is usually located in the same room as the operating or surgical table T, such as at the side of a table on which patient P is located. It is to be understood, however, that operator O can be located in a different room or a completely different building from patient P. That is, one or more user control systems 106 may be collocated with the manipulator assemblies 102, or the user control systems may be positioned in separate locations. Multiple user control systems allow more than one operator to control one or more robotically-assisted manipulator assemblies in various combinations.

User control system 106 generally includes one or more input devices for controlling manipulator assembly 102. The input devices may include any number of a variety of devices, such as joysticks, trackballs, data gloves, trigger-guns, hand-operated controllers, voice recognition devices, body motion or presence sensors, and/or the like. To provide operator O a strong sense of directly controlling medical instrument 104, the input devices may be provided with the same degrees of freedom as the associated medical instrument 104. In this manner, the input devices provide operator O with telepresence and the perception that the input devices are integral with medical instrument 104.

Manipulator assembly 102 supports medical instrument 104 and may include a kinematic manipulator support structure of one or more non-servo controlled linkages (e.g., one or more links that may be manually positioned and locked in place), and/or one or more servo controlled linkages (e.g., one or more links that may be controlled in response to commands from a control system), and an instrument holder. Manipulator assembly 102 may optionally include a plurality of actuators or motors that drive inputs on medical instrument 104 in response to commands from the control system (e.g., a control system 110). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to system 100 describing the rotation and orientation of the motor shafts. This position sensor data may be used to determine motion of the objects manipulated by the actuators. The manipulator assembly 102 may position its held instrument 104 so that a pivot point occurs at the instrument's entry aperture into the patient. The pivot point may be referred to as a remote center of manipulation. The manipulator assembly 102 may then manipulate its held instrument so that the instrument may be pivoted about the remote center of manipulation, inserted into and retracted out of the entry aperture, and rotated about its shaft axis.

System 100 also includes a display system 108 for displaying an image or representation of the surgical site and medical instrument 104. Display system 108 and user control system 106 may be oriented so operator O can control medical instrument 104 and user control system 106 with the perception of telepresence. In some examples, the display system 108 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

System 100 also includes control system 110. Control system 110 includes at least one memory 114 and at least one computer processor 112 for effecting control between medical instrument 104, user control system 106, and display system 108. Control system 110 also includes programmed instructions (e.g., a non-transitory machine-readable medium storing the instructions) to implement some or all of the methods described in accordance with aspects disclosed herein, including instructions for providing information to display system 108. While control system 110 is shown as a single block in the simplified schematic of FIG. 1, the system may include two or more data processing circuits with one portion of the processing optionally being performed on or adjacent to manipulator assembly 102, another portion of the processing being performed at user control system 106, and/or the like. The processors of control system 110 may execute instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, control system 110 supports wireless communication protocols such as Bluetooth, IrDA, HomeRF, IEEE 802.11, DECT, and Wireless Telemetry.

Movement of a manipulator assembly 102 may be controlled by the control system 110 so that a shaft or intermediate portion of instruments mounted to the manipulator assemblies 102 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, excessive lateral motion of the shaft that might otherwise tear the tissues adjacent the aperture or enlarge the access site inadvertently is inhibited. Some or all of such constraint on the motions of the manipulator assemblies 102 at the access sites may be imposed using mechanical manipulator joint linkages that inhibit improper motions, or may in part or in full be imposed using data processing and control techniques. In some embodiments, control system 110 may receive force and/or torque feedback from medical instrument 104. Responsive to the feedback, control system 110 may transmit signals to user control system 106. In some examples, control system 110 may transmit signals instructing one or more actuators of manipulator assembly 102 to move medical instrument 104.

Figure 2:
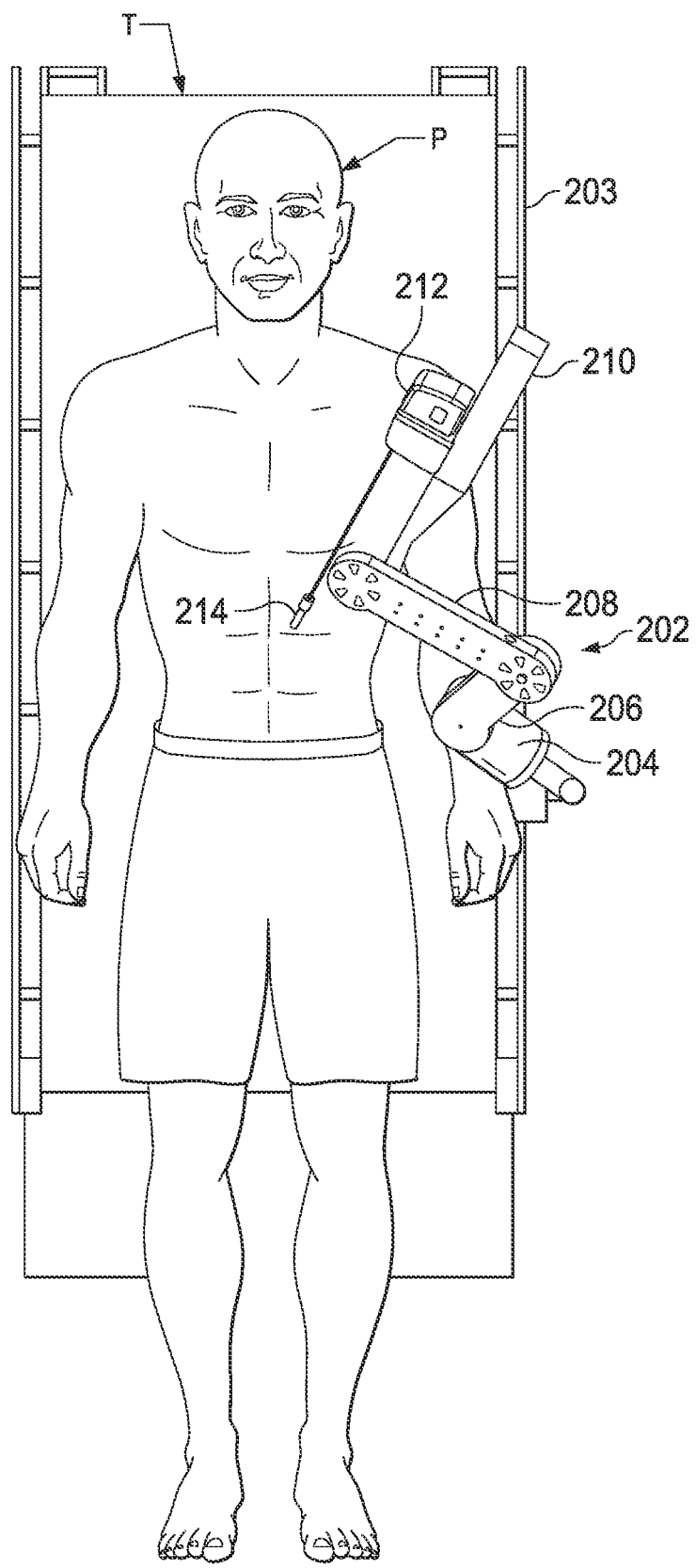
FIG. 2 illustrates a manipulator assembly mounted to a surgical table according to some embodiments.

FIG. 2 illustrates a manipulator assembly 202 mounted to a side rail 203 of the surgical table T according to some embodiments. In this embodiment, the manipulator assembly 202 includes a base linkage arm 204 rotatably coupled to a linkage arm 206. The linkage arm 206 is rotatably coupled to a linkage arm 208 which is rotatably coupled to an instrument holder 210. A medical instrument 212 is mounted to the instrument holder and is manipulatable by the manipulator assembly 202 to perform a procedure on the patient P.

FIGS. 3 and 4 illustrate a hardware-constrained remote center manipulator assembly 300 (e.g., 102, 202) in accordance with many embodiments. The manipulator assembly 300 includes a linkage assembly 302 including a support link 303, a base linkage arm 304, a linkage arm 306, and a linkage arm 308. The manipulator assembly 300 also includes an instrument holder 310 configured to support a detachable surgical instrument 312. A cannula 314 is removably mounted to the instrument holder 310 such that the cannula 314 is rigidly mounted to a lower portion of the instrument holder 310 when attached. An opening in the cannula 314 is sized for passage of a shaft of the instrument 312 through the opening for insertion of a distal (toward the patient) portion of the instrument 312 into a patient P. In many embodiments, the support link 303 may be held in a fixed position relative to a patient P being operated on with the manipulator assembly 300. For example, the support link 303 may be rigidly mounted to the table T, to a cart placed near the table T, or to a floor stand, and in some embodiments, the support link 303 may be supported by movable set-up arms/joints. A joint 316 between the support link 303 and the base linkage arm 304 allows rotation of the base linkage arm 304 around an axis A1 that intersects a remote center of motion RC. The remote center of motion RC may be located coincident with a portion of the cannula 314 through which the instrument 312 passes, and in some embodiments, may be coincident with a longitudinal axis of the cannula 314.

The linkages of the manipulator assembly 300 distal of the link 303 are configured to provide selective movement of the instrument holder 310 that is limited to two-dimensional rotation of the instrument holder 310 about the remote center RC. With respect to a direction of rotation of the instrument holder 310 about the remote center RC, referred to herein as pitch, the instrument holder 310 and the linkage arms 306, 308 are coupled so as to form a parallelogram linkage that provides movement of the instrument holder 310 that is limited to rotation about the remote center RC around an axis A2 (see FIG. 9A) that is substantially perpendicular to the axis A1 and to a plane extending along an extension direction of base linkage arm 304 (see axis A2 in the perspective view of FIG. 9A). In the orientation depicted in FIG. 3, the pitch direction about the remote center is substantially perpendicular to the depicted Z axis and to the XY plane. The linkage arm 306 has a proximal end that is rotationally coupled with a distal end of the base linkage arm 304 via a joint 318. The linkage arm 308 has a proximal end that is rotationally coupled with a distal end of the linkage arm 306 via a joint 320. The instrument holder 310 is coupled with a distal end of the linkage arm 308 via a joint 322. The joints 320, 322 are rotationally driven by rotation of the first joint 318 so that the linkage arm 306, the linkage arm 308, and the instrument holder 310 form the parallelogram linkage. In the position shown, the linkage arm 306 defines a first parallelogram side 330 extending between the first and second parallelogram joints 318, 320; the linkage arm 308 defines a second parallelogram side 332 extending between the joints 320, 322; and the instrument holder 310 defines a third parallelogram side 334 extending between the joint 322 and the remote center RC. Rotation of the linkage arm 306 relative to the base linkage arm 304 serves to move the instrument holder 310 so that the distal end of the third parallelogram side 334 remains coincident with the remote center of manipulation RC, thereby pitching the instrument holder 310 about the axis A2 (See axis A2 in the perspective view of FIG. 9A) substantially perpendicular to the axis A1.

Any suitable approach can be used to rotationally couple the joint 318, the joint 320, and the joint 322. For example, linkage arm 306 may include a pulley or pulley assembly 340 coupled to joint 318 that is rotationally fixed to base linkage arm 304 and rotatable relative to linkage arm 306. The linkage arm 306 may also include a pulley or pulley assembly 342 coupled to joint 320 that is rotationally fixed to linkage arm 308 and rotatable relative to linkage arm 306. The rotation of the pulley assembly 340 may be tied to rotation of the pulley assembly 342, for example by one or more drive member sections (e.g., cable sections, belt sections, or any other suitable drive member). By tying the rotation of pulley assemblies 340 and 342, the rotation of the linkage arm 308 about the joint 320 may be coupled and driven by the rotation of linkage arm 306 relative to the base linkage arm 304, such that the relative angular orientation between the linkage arm 308 and the linkage arm 306 will be tied to the relative angular orientation between the linkage arm 306 and the base linkage arm 304. In another example, the linkage arm 308 may include a pulley or pulley assembly 344 (coaxial with the pulley assembly 342, which is substantially along the axis Z in the orientation in FIG. 3) coupled to joint 320 that is rotationally fixed to linkage arm 306 and rotatable relative to linkage arm 308. The linkage arm 308 may also include a pulley or pulley assembly 346 coupled to joint 322 that is rotationally fixed to the instrument holder 310 and rotatable relative to linkage arm 308. The rotation of the pulley assembly 344 may be tied to rotation of the pulley assembly 346, for example by one or more drive member sections (e.g., cable sections, belt sections, or any other suitable drive member). By tying the rotation of pulley assemblies 344 and 346, the rotation of the instrument holder 310 about the joint 322 may be coupled and driven by the rotation of linkage arm 308 relative to the linkage arm 306, such that the relative angular orientation between the instrument holder 310 and the linkage arm 308 will be tied to the relative angular orientation between the linkage arm 308 and the linkage arm 306. Motion of the linkage 306 may be driven by an actuator 343, such as a motor, to drive the parallelogram linkage about the remote center RC.

FIG. 5A illustrates one embodiment of the pulley assemblies 342 and 344. In the embodiment of FIG. 5A, pulley assembly 342A includes a pulley 356A to which a drive belt section 358A is attached (e.g., in a first tensile direction) and a pulley 360A to which a drive belt section 362A is attached (e.g., in a second tensile direction that is opposite to the first tensile direction). Pulley assembly 344A includes a pulley 364A to which a drive belt section 366A is attached (e.g., in the first tensile direction) and a pulley 368A to which a drive belt section 370A is attached (e.g., in the second tensile direction). In this embodiment, each linkage arm includes a pair of side-by-side pulleys. In this embodiment the width W1 of the linkage arm 308 and the width W2 of the linkage arm 306 must be wide enough to accommodate the side-by-side pulleys. With wide linkage arms, the joint 322 may be located farther away from the remote center of manipulation RC to provide clearance for neighboring manipulator assemblies and user access to manipulator assemblies and the patient. Consequently, the wide linkage arms may result in longer (and thus heavier) linkage arms that may require heavier and stronger motors for actuation.

For some surgical approaches or when the manipulator assembly is desired to be positioned close to the patient, a compact manipulator assembly may be suitable. For example, when the manipulator assembly 300 is configured for coupling to a rail of an operating table T, the assembly may have shorter linkage arms and have a lighter weight than manipulator assemblies that are coupled to a common chassis that is positioned further from the table. The manipulator assembly 300 may have a compact design by configuring the joint 322 to be close to the remote center of manipulation RC. In this embodiment, the linkage arm 308 may be coupled to a portion (e.g., side) of the instrument holder 310 near the cannula 314 to locate the joint 322 close to the remote center of manipulation RC. As a distance D3 between the joint 322 and the remote center of manipulation RC is minimized, the length D1 of the linkage arm 306 between the joints 318 and 320 becomes minimized. A distance D2 between the joints 320 and 322 may also be minimized to reduce the weight of the linkage arm 308. Such compact and lighter weight assemblies may also be used for non-table mounted assemblies, such as cart-mounted assemblies.

With the joint 322 moved closer to the remote center of manipulation RC and the linkage arm 308 coupled to the side of the instrument holder 310, reducing the width W1 of the linkage arm 308 and the width W2 of the linkage arm 306 would provide greater clearance for neighboring manipulator assemblies and user access to the manipulator assemblies and the patient. FIG. 5B illustrates another embodiment of the pulley assemblies 342 and 344. In this embodiment, a nested track pulley configuration allows for a narrower profile linkage arm, as compared to the side-by-side pulley configuration of FIG. 5A. In the embodiment of FIG. 5B, pulley assembly 342B includes a pulley 356B to which a drive belt section 358B is attached. In this embodiment, a nested drive belt section (not shown in this view)

may attach to an inner pulley track of pulley 356B as will be described in greater detail below. Pulley assembly 344B includes a pulley 364B to which a drive belt section 366B is attached. In this embodiment, a nested drive belt section may attach to an inner pulley track of pulley 364B as will be described in detail below. In this embodiment, each linkage arm includes a pair of nested pulley tracks. In this embodiment the width W1 of the linkage arm 308 and the width W2 of the linkage arm 306 may be just wide enough to accommodate the width of a single drive belt section. In this embodiment, the width W1 and W2 may be, for example, approximately 0.810 inches. In other embodiments, a linkage arm accommodating the width of a single drive belt section may be less than 1.0 inches or less than 0.50 inches. In some embodiments, the linkage arm may be wider or narrower, depending on the width of the single drive belt section. With narrower linkage arms, the joint 322 may be located closer to the remote center of manipulation RC while still providing clearance for neighboring manipulator assemblies and user access to manipulator assemblies and the patient. Consequently, the narrower linkage arms may result in shorter (and thus lighter) linkage arms that may accommodate smaller, more lightweight motors for actuation. In some embodiments, the distance D1 between the joints 318, 320 may be approximately 5.9 inches, but in other embodiments may be longer or shorter. In some embodiments, the distance D2 between the joints 320, 322 may be approximately 10.0 inches, but in other embodiments may be longer or shorter. The belt sections described herein are examples of drive member sections that may be used to effectuate movement of the parallelogram linkage arms. In alternative examples, the drive member sections may include mechanical cables, chains, and/or other suitable drive members. For example, in some embodiments, pulley assemblies 342 and 344 may include nested drive cable sections instead of nested drive belt sections. Further, the various embodiments of FIGS. 6-13 are described below using belt sections and/or belt tracks as examples. However, such embodiments may use alternative drive member sections and associated drive tracks. For example, the embodiments described herein may use cable sections and cable tracks. Further, in various embodiments, the drive member sections may include more than one type of drive member, for example, using a cable section for one drive member section and a belt section for another drive member section.

FIG. 6 illustrates a manipulator transmission system 400 that may be used, for example, within the linkage arm 306. The manipulator transmission system 400 includes the pulley 342 (e.g., a first pulley), the pulley 340 (e.g., a second pulley), a drive belt section 402 (e.g., a first drive member section) having a distal end 401 and a proximal end 403, and a drive belt section 404 (e.g., a second drive member section) having a distal end 405 and a proximal end 407. The drive belt section 402 is attached at its distal end 401 to pulley 342 and wraps around an outer belt track 406 (e.g., a first drive track) of the pulley 342. The drive belt section 402 is also attached at its proximal end 403 to pulley 340 and wraps around an outer belt track 408 (e.g., a first drive track) of the pulley 340. The drive belt section 404 is attached at its distal end 405 to pulley 342 and wraps around an inner belt track 410 (e.g., a second drive track). The drive belt section 404 is also attached at its proximal end 407 to pulley 340 and wraps around an inner belt track 412 (e.g., a second drive track). The drive belt section 402 is wound around pulley 340 in a first tensile direction T1, and a drive belt section 404 is wound around pulley 340 in a second tensile direction T2, with the first tensile direction T1 being opposite to the second tensile direction T2. In the example orientation depicted in FIG. 6, drive belt section 402 is subject to an increased tensile force in the tensile direction T1 when the linkage arm 306 is rotated counter-clockwise about the joint 318, and drive belt section 404 is subject to an increased tensile force in the tensile direction T2 when the linkage arm 306 is rotated clockwise about the joint 318. It should be appreciated that tensile directions T1 and T2 are provided by way of example and that the pulleys 340 and 342 may be alternatively configured, for example, such that an outer drive belt section is subject to an increased tensile force when the linkage arm 306 rotates clockwise about the joint 318 and that an inner drive belt section is subject to an increased tensile force when the linkage arm 306 rotates counter-clockwise about the joint 318. In various embodiments, the drive belt sections may be subject to intrinsic tensions when in a static, motionless state. The intrinsic tensions may be due to, for example, component weight, gravitational effects, and/or pre-tensions applied during an assembly process.

FIG. 7A provides a perspective view of the pulley 342 of the manipulator transmission system 400. In this embodiment, the pulley 342 includes a pulley body 418 including a pulley component 420 and a pulley component 422 extending from the pulley body. The pulley component 420 and the pulley component 422 may be concentric and may be arranged around an inner opening of the pulley 342, with pulley component 420 arranged outside of pulley component 422. For example, pulley component 420 may circumferentially surround at least a portion of the circumference of pulley component 422. The outer belt track 406 extends along an outer surface (e.g., circumference) of the pulley component 420, and the inner belt track 410 extends along an outer surface (e.g., circumference) of the pulley component 422. Optionally, in some embodiments, the outer belt track 406 and the inner belt track 410 are substantially co-planar with a plane P1. In some embodiments, the outer belt track 406 and the inner belt track 410 are offset from one another and are not coplanar. The distal end 401 of the drive belt section 402 may be attached to pulley component 420 in any of a variety of ways. In this embodiment, the drive belt section 402 may include a belt anchor 424 that lodges within a groove 421 in the pulley component 420 to couple the drive belt section 402 to the pulley 342. The distal end 405 of the drive belt section 404 may be attached to pulley component 422 in any of a variety of ways. In this embodiment, the drive belt section 404 may include a belt anchor 426 that lodges within a groove 423 to couple the drive belt section 404 to the pulley 342. In alternative embodiments, the drive belt sections may be coupled to the pulleys by welded connections, chemical adhesives, screws, snaps, clamps, rivets, tabs, tapes, elastomeric bands, or other suitable connection systems. The drive belt section 404 extends from the groove 423 and around the inner belt track 410 and nests between the pulley components 420, 422. In this embodiment, the outer belt track 406 and the inner belt track 410 may be separated by an abutment surface 430 with a curved profile. When the drive belt section 404 is fully wound around the inner belt track 410, the abutment surface 430 may abut or be proximate to the drive belt section 404. In this embodiment, the outer belt track 406 may terminate at an abutment surface 432. When the drive belt section 402 is fully wound around the outer belt track 406, the abutment surface 432 may abut or be proximate to the drive belt section 404. In the embodiment of FIG. 7A, a radius r1 of the pulley component 422 and a radius r2 of the pulley component 420 may be uniform. In alternative embodiments, the radii of the pulley components and/or the radii of the belt or drive track profiles may be variable to maintain proportional motion of the instrument holder or to modify an acceleration of manipulator components. Pulley 340 of the manipulator transmission system 400 may be substantially similar to pulley 342 with similar attachment for drive belt sections 402, 404

FIG. 7B provides a perspective view of an alternative pulley 450 of the manipulator transmission system that may be substantially the same as the pulley 342 with the differences as provided. In this embodiment, the pulley 450 includes a pulley body 468 including a pulley component 470 and a pulley component 472 extending from the pulley body. The pulley component 470 and the pulley component 472 may be concentric and may be arranged around an inner opening of the pulley 450, with pulley component 470 arranged outside of pulley component 472. For example, pulley component 470 may circumferentially surround at least a portion of the circumference of pulley component 472. An outer belt track 456 extends along an outer surface (e.g., circumference) of the pulley component 470, and an inner belt track 460 extends along an outer surface (e.g., circumference) of the pulley component 472. The outer belt track 456 and the inner belt track 460 are substantially co-planar with a plane P1. The distal end 401 of the drive belt section 402 may be attached to pulley component 420 in any of a variety of ways. In this embodiment, the belt anchor 424 lodges within a groove 471 in the pulley component 470 to couple the drive belt section 402 to the pulley 450. The distal end 405 of the drive belt section 404 may be attached to pulley component 472 in any of a variety of ways. In this embodiment, the belt anchor 426 lodges within a groove 473 to couple the drive belt section 404 to the pulley 450. The drive belt section 404 extends from the groove 473 and around the inner belt track 460 and nests between the pulley components 470, 472. In this embodiment, the inner belt track 460 may be substantially continuous (e.g., in the shape of a cylinder) except for the opening to the groove 423 and may be non-continuous with the outer belt track 456. In this embodiment, the outer belt track 456 may be partially continuous (e.g. a partial cylinder) with abutment surfaces 480, 482. When the drive belt section 404 is fully wound around the inner belt track 460, the abutment surface 480 may abut or be proximate to the drive belt section 404. When the drive belt section 402 is fully wound around the outer belt track 456, the abutment surface 482 may abut or be proximate to the drive belt section 404. In the embodiment of FIG. 7B, a radius r3 of the pulley component 472 and a radius r4 of the pulley component 470 may be uniform. In alternative embodiments, the radii of the pulley components may be variable to maintain proportional motion of the instrument holder or to modify an acceleration of manipulator components. A pulley substantially similar to pulley 450 may be paired with the pulley 450 in the manipulator transmission system 400, in the same way that pulley 342 is paired with pulley 340. In some embodiments, the pulley 342 and the pulley 450 may be paired in the manipulator transmission system 400.

In alternative embodiments, the outer belt track (e,g, belt track 406) and the outermost drive belt section (e.g. drive belt section 402) may be located within grooves, similar to belt track 410 and drive belt section 404. In other words, a component wall may extend from the pulley body (e.g. pulley body 418) to provide a circumferential cover for all or a portion of the outer belt track and the outermost drive belt section.

FIG. 8A is a perspective view of the manipulator assembly 300 in a retracted configuration according to some embodiments. FIG. 8B is a perspective view of the manipulator transmission system 400 of the manipulator assembly 300 in the retracted configuration according to some embodiments. In some embodiments of the retracted configuration, the drive belt section 404 may be circumferentially fully wound or at an otherwise maximum winding around the inner belt track 410 of pulley 342, with the abutment surface 430 being in abutment with or proximate to a portion 435 of the drive belt section 404 tangential to the inner belt track 410. In the retracted configuration, the drive belt section 402 may be circumferentially fully wound or at an otherwise maximum winding around the outer belt track 408 of pulley 340, with the abutment surface 436 being in abutment with or proximate to a portion 437 of the drive belt section 404 tangential to the inner belt track 412.

FIG. 9A is a perspective view of the manipulator assembly 300 in a partially extended configuration according to some embodiments. FIG. 9B is a perspective view of the manipulator transmission system 400 of the manipulator assembly 300 in the partially extended configuration according to some embodiments. To move from the retracted configuration of FIG. 8A to the partially extended configuration of FIG. 9A, the actuator 343 coupled to the linkage arm 306 may rotate the linkage arm 306 in the clockwise direction R3 about the joint 318, increasing tension (as compared to a motionless state) in the drive belt section 404 in the tensile direction T2. As compared to the retracted configuration, in the partially extended configuration, the drive belt section 404 may have a lesser amount of winding around the inner belt track 410 of pulley 342, with the abutment surface 430 being farther away from the portion 435 of the inner drive belt section 404 tangential to the inner belt track 410. The drive belt section 402 may also have a lesser amount of winding around the outer belt track 408 of pulley 340, with the abutment surface 436 being farther away from the portion 437 of the drive belt section 404 tangential to the inner belt track 412. As the linkage arm 306 extends to the partially extended configuration by rotating clock-wise from the fully retracted configuration, the drive belt section 402 wraps on to the outer belt track 406 of the pulley 342 and unwraps from the outer belt track 408 of the pulley 340. Also, as the linkage arm 306 extends, the drive belt section 404 unwraps from the inner belt track 410 of the pulley 342 and wraps on to the inner belt track 412 of the pulley 340.

FIG. 10A is a perspective view of the manipulator assembly 300 in an extended configuration according to some embodiments. FIG. 10B is a perspective view of the manipulator transmission system 400 of the manipulator assembly 300 in the extended configuration according to some embodiments. To move from the partially extended configuration of FIG. 9A to the extended configuration of FIG. 10A, the actuator 343 coupled to the linkage arm 306 may continue rotation of the linkage arm 306 in the clockwise direction R3, increasing tension (as compared to a motionless state) in the drive belt section 404 in the tensile direction T2. In some embodiments of the extended configuration, the drive belt section 404 may be fully wound or at an otherwise maximum winding around the inner belt track 412 of pulley 340, such that an abutment surface 434 is in abutment with or proximate to the portion 437 of the drive belt section 404 tangential to the inner belt track 412. The outer drive belt section 402 may be fully wound or at an otherwise maximum winding around the outer belt track 406 of pulley 342, such that the abutment surface 432 is in abutment with or proximate to the portion 435 of the drive belt section 404 tangential to the inner belt track 410. As the manipulator assembly 300 moves to the extended configuration from the partially extended configuration, the drive belt section 402 wraps further on to the outer belt track 406 of the pulley 342 and unwraps further from the outer belt track 408 of the pulley 340. Also, the drive belt section 404 unwraps further from the inner belt track 410 of the pulley 342 and wraps further on to the inner belt track 412 of the pulley 340.

As shown in the schematic cross-sectional view of FIG. 11, pulley 342 is fixed both rotationally and translationally with respect to linkage arm 308. Pulley 344 is fixed rotationally and translationally with respect to linkage arm 306. More specifically, a coupling extension 350 of the linkage arm 306 extends into the linkage arm 308 to fixedly couple the pulley 344 to the linkage arm 306 such that the pulley 344 moves with the linkage arm 306. A coupling extension 352 of the linkage arm 308 extends into the linkage arm 306 to fixedly couple the pulley 342 to the linkage arm 308 such that the pulley 342 moves with the linkage arm 308.

As the linkage arms 306, 308 are pitched forward or backward, the instrument holder 310 and cannula 314 rotate about the axis A2 through the remote center of manipulation RC. To return the linkage arms 306, 308 to the retracted configuration from the partially extended configuration, the actuator 343 may rotate the linkage arm 306 in a counter-clockwise direction, thus causing a reverse rotation of the pulleys and linkage arms described above.

The drive belt section 402 and the drive belt section 404 may be a discrete belt sections such that the distal end 401 is not continuous with or directly coupled to the distal end 405. Similarly, the proximal end 403 is not continuous with or directly coupled to the proximal end 407. FIG. 12 illustrates an alternative embodiment of a manipulator transmission system 500 in which an outer drive belt section 502 is continuous with an inner drive belt section 504. In this embodiment, the outer drive belt section 502 and the inner drive belt section 504 are portions of a single continuous drive belt 506. The drive belt 506 may include an end 508 terminating on an outer belt track of pulley 520 (e.g. pulley 342) and an end 510 terminating on an inner belt track of pulley 520. At a redirection guide 524 (e.g., a pin), the drive belt 506 is routed off of the outer belt track of pulley 522 and onto an inner belt track. At a redirection guide 526 (e.g., a pin), the drive belt 506 wraps again around the inner belt track and extends out of the pulley 522. With a single drive belt, two belt anchors may be eliminated in the pulley 522. Since welding at the belt anchors is a potential point of failure, eliminating at least some belt anchors may improve the reliability of the manipulator transmission system. However, with a single drive belt, the belt follows a tight-radius serpentine path which may generate stresses in the belt and limit belt life. In an alternative embodiment, the outer drive belt section 502 and the inner drive belt section 504 may be two separate drive belt sections that are coupled at a common point such as the redirection guide 526 or at within a groove (e.g., groove 473).

FIG. 13 illustrates a method 600 for operating a manipulator transmission system (e.g., manipulator transmission system 400) according to some embodiments. The method 600 is illustrated as a set of operations or processes 602 through 608 and is described with continuing reference to FIGS. 1-11. Not all of the illustrated processes may be performed in all embodiments of method 600. Additionally, one or more processes that are not expressly illustrated in FIG. 12 may be included before, after, in between, or as part of the processes 602 through 608. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by the control system 110.

At a process 602, a first linkage arm (e.g. linkage arm 306) may be rotated by rotating an actuator coupled to the first linkage arm (e.g., actuator 343). At a process 604, a first belt section is wound on to a first belt track of the first pulley. For example, rotation of the linkage arm 306 causes the drive belt section 404 to become wound on the inner belt track 412 of pulley 340. At a process 606, a second belt section is unwound from a second belt track of the first pulley. For example, as the drive belt section 404 is becoming wound on the inner belt track 412, the drive belt section 402 becomes unwound from the outer belt track 408 of the pulley 340. At a process 608, a linkage assembly comprising the first linkage arm is operated to rotate an instrument holder about an axis that intersects a remote center of manipulation. For example, the linkage assembly 302 which includes the linkage arms 306, 308, rotates the instrument holder 310 with cannula 314 about the axis A2 through the remote center of manipulation RC, as a result of the actuator 343 rotating the pulley 340.

One or more elements in embodiments of this disclosure may be implemented in software to execute on a processor of a computer system such as a control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus, and various systems may be used with programs in accordance with the teachings herein. The required structure for a variety of the systems discussed above will appear as elements in the claims. In addition, the embodiments of the invention are not described with reference to any particular programming language. It will be appreciated that a variety of programming languages may be used to implement the teachings of the invention as described herein.

In the above description, specific details describe some embodiments consistent with the present disclosure. Numerous specific details are set forth in order to provide a thorough understanding of the embodiments. It will be apparent to one skilled in the art, however, that some embodiments may be practiced without some or all of these specific details. The specific embodiments disclosed herein are meant to be illustrative but not limiting. One skilled in the art may realize other elements that, although not specifically described, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, components, and circuits have not been described in detail so as not to unnecessarily obscure aspects of the embodiments.

In the above description, the singular forms "a", "an", and "the" are intended to include the plural forms as well, unless the context indicates otherwise. And the terms "comprises," "comprising," "includes," "has," and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. The auxiliary verb "may" likewise implies that a feature, step, operation, element, or component is optional.

Although some of the examples described herein refer to surgical procedures or instruments, or medical procedures and medical instruments, the techniques disclosed optionally apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical medical treatment or diagnosis procedures.

Further, although some of the examples presented in this disclosure discuss teleoperational robotic systems or remotely operable systems, the techniques disclosed are also applicable to computer-assisted systems that are directly and manually moved by operators, in part or in whole.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

What is claimed is:

1. A surgical manipulator linkage assembly comprising:
a linkage arm comprising:
a first pulley and a second pulley, wherein each of the first pulley and the second pulley comprise a first drive track and a second drive track, wherein the first drive track and the second drive track are substantially co-planar, with the first drive track extending at least partially around the second drive track;
a first drive member section extending between the first drive tracks of the first pulley and the second pulley; and
a second drive member section extending between the second drive tracks of the first pulley and the second pulley,
wherein the first drive member section is wound around the first pulley in a first tensile direction and the second drive member section is wound around the first pulley in a second tensile direction opposite to the first tensile direction.

2. The surgical manipulator linkage assembly of claim 1, wherein the first drive track of the first pulley is concentric with the second drive track of the first pulley.

3. The surgical manipulator linkage assembly of claim 1, wherein the first drive member section comprises a first belt section and the second drive member section comprises a second belt section, and wherein the first pulley includes a first belt anchor configured to retain an end portion of the first belt section in the first pulley.

4. The surgical manipulator linkage assembly of claim 1, wherein the first drive member section is directly coupled to the second drive member section.

5. The surgical manipulator linkage assembly of claim 1, wherein the first drive member section and the second drive member section each comprise at least one selected from the group consisting of belts, cables, and chains.

6. The surgical manipulator linkage assembly of claim 1, further comprising a joint coupled to the linkage arm and configured to rotate an instrument holder.

7. The surgical manipulator linkage assembly of claim 1, further comprising a linkage assembly including the linkage arm, which is a first linkage arm, and a second linkage arm coupled to the first linkage arm.

8. The surgical manipulator linkage assembly of claim 7, wherein the second linkage arm comprises:
a third pulley and a fourth pulley, wherein each of the third pulley and the fourth pulley comprise a third drive track and a fourth drive track, wherein the third drive track and the fourth drive track are substantially co-planar;
a third drive member section extending between the third drive tracks of the third pulley and the fourth pulley; and
a fourth drive member section extending between the fourth drive tracks of the first pulley and the fourth pulley,
wherein the third drive member section is wound around the third pulley in a third tensile direction and the fourth drive member section is wound around the third pulley in a fourth tensile direction opposite to the third tensile direction.

9. The surgical manipulator linkage assembly of claim 8, wherein the second and third pulleys are rotatable about a common axis.

10. The surgical manipulator linkage assembly of claim 8, wherein the third drive track of the third pulley is concentric with the fourth drive track of the third pulley.

11. A surgical manipulator linkage assembly comprising:
a linkage arm comprising:
a first pulley and a second pulley, wherein each of the first pulley and the second pulley includes an outer drive track and an inner drive track nested within the outer drive track;

a first drive member section extending between the inner drive tracks of the first pulley and the second pulley; and a second drive member section extending between the outer drive tracks of the first pulley and the second pulley, wherein rotation of the first pulley in a first direction causes a rotation of the second pulley in the first direction, and wherein rotation of the first pulley in a second direction causes a rotation of the second pulley in the second direction.

12. The surgical manipulator linkage assembly of claim 11, wherein the inner drive track and the outer drive track are substantially co-planar.

13. The surgical manipulator linkage assembly of claim 11, wherein the first drive member section comprises a first belt section and the second drive member section comprises a second belt section, and wherein the first pulley includes a first belt anchor configured to retain an end portion of the first belt section.

14. The surgical manipulator linkage assembly of claim 11, wherein the first drive member section is directly coupled to the second drive member section.

15. The surgical manipulator linkage assembly of claim 11, wherein the first drive member section and the second drive member section each comprise at least one selected from the group consisting of belts, cables, and chains.

16. The surgical manipulator linkage assembly of claim 11, further comprising a joint coupled to the linkage arm and configured to rotate an instrument holder.

17. The surgical manipulator linkage assembly of claim 11, further comprising a linkage assembly including the linkage arm, which is a first linkage arm, and a second linkage arm coupled to the first linkage arm.

18. The surgical manipulator linkage assembly of claim 17, wherein the second linkage arm comprises:

a third pulley and a fourth pulley, wherein each of the third pulley and the fourth pulley includes an outer drive track and an inner drive track nested within the outer drive track;

a third drive member section extending between the inner drive tracks of the third pulley and the fourth pulley; and a fourth drive member section extending between the outer drive tracks of the third pulley and the fourth pulley, wherein rotation of the third pulley in a third direction causes a rotation of the fourth pulley in the third direction, and wherein rotation of the third pulley in a fourth direction causes a rotation of the fourth pulley in the fourth direction.

19. The surgical manipulator linkage assembly of claim 18, wherein the second and third pulleys are rotatable about a common axis.

20. The surgical manipulator linkage assembly of claim 18, wherein the inner drive track and the outer drive track of the third pulley are substantially co-planar.

* * * * *